United States Patent [19]
Laske et al.

[11] Patent Number: 6,038,463
[45] Date of Patent: Mar. 14, 2000

[54] MEDICAL ELECTRICAL LEAD

[75] Inventors: Timothy G. Laske, Shoreview; Jon M. Ocel, New Brighton, both of Minn.

[73] Assignee: Medtronic, Inc., Minneapolis, Minn.

[21] Appl. No.: 08/938,238

[22] Filed: Sep. 26, 1997

[51] Int. Cl.[7] .............................. A61N 1/05; A61B 5/042
[52] U.S. Cl. ..................... 600/374; 600/375; 607/119; 607/122; 607/127; 607/131
[58] Field of Search ..................... 600/372, 373, 600/374, 375, 376, 377, 381; 607/116, 119, 122, 126–128, 131; 606/41

[56] References Cited

U.S. PATENT DOCUMENTS

| | | |
|---|---|---|
| 4,106,512 | 8/1978 | Bisping . |
| 4,972,848 | 11/1990 | DiDomenico et al. . |
| 5,231,996 | 8/1993 | Bardy et al. . |
| 5,246,014 | 9/1993 | Williams et al. . |
| 5,354,327 | 10/1994 | Smits . |
| 5,385,578 | 1/1995 | Bush et al. ............................ 607/122 |
| 5,569,883 | 10/1996 | Walter et al. ........................... 607/122 |
| 5,584,873 | 12/1996 | Shoberg et al. . |
| 5,676,694 | 10/1997 | Boser et al. ............................ 607/122 |
| 5,851,227 | 12/1998 | Spehr ..................................... 607/122 |

*Primary Examiner*—Linda C. M. Dvorak
*Assistant Examiner*—David M. Ruddy
*Attorney, Agent, or Firm*—Reed A. Duthler; Harold R. Patton

[57] ABSTRACT

An implantable electrical lead of the type having a rigid, insulative electrode head carrying an advanceable helical electrode. The electrode head is mounted to an elongated insulative lead body less rigid than said electrode head and which carries an extensible conductor coupled to the helical electrode and an inextensible conductor mechanically coupled to the proximal end of the lead. A second electrode is mounted to said lead body adjacent the electrode head and is coupled to the inextensible conductor. The inextensible electrical conductor is mechanically coupled to the electrode head such that poximally directed traction forces applied to the proximal end of the lead body are applied to the head by the inextensible conductor and not by the second electrode.

8 Claims, 6 Drawing Sheets

MEDICAL ELECTRICAL LEAD

BACKGROUND OF THE INVENTION

The present invention relates generally to implantable medical leads and more specifically to leads with rigid electrode head assemblies.

Screw-in leads of the type provided with advancable fixation devices such as screws or barbs generally are provided with relatively rigid electrode head members provided with internal lumens housing the advancable fixation devices. Particularly in the context of screw-in leads, it is common to use a coiled conductor, coupled to a rotatable fixation helix which also serves as a pacing electrode. Such leads are illustrated in U.S. Pat. No. 4,106,512 issued to Bisping. In bipolar screw-in leads, a ring electrode may also be mounted to the electrode head, as illustrated in U.S. Pat. No. 5,354,327 issued to Smits. In both unipolar and bipolar leads, the relatively rigid electrode head is typically coupled to a substantially more elastic lead body carrying both a the coiled conductor coupled to the fixation helix and the conductor coupled to the ring electrode.

It is sometimes necessary to remove a chronically implanted lead, which may be adhered to the heart by fibrotic tissue growth. For purposes of improved extractability, it has long been recognized that it is desirable to reinforce leads by providing an inextensible or only slightly extensible member extending the length of the lead body to prevent separation of the distal end of the lead body during application of traction to the proximal end of the lead body. Several such reinforcement mechanisms are disclosed in U.S. Pat. No. 5,231,996 issued to Bardy et al. A separate reinforcing member is not necessary if the conductor coupled to the distal or tip electrode of the lead is coupled to an inextensible conductor, as in U.S. Pat. No. 5,246,014, issued to Williams et al. This expedient is, unfortunately, not readily available in the case of a lead in which rotation of the fixation helix is accomplished by means of the conductor. In order to provide torque transfer, such leads typically employ coiled conductors, as noted above, which are inherently extensible. The presence of the coil conductor typically will not prevent separation of the lead body from the electrode head as a result of traction applied to the proximal end of the lead.

SUMMARY OF THE INVENTION

The present invention is intended to provide a lead of the type employing an extensible conductor coupled to an electrode mounted in a relatively rigid electrode head assembly which resists separation of the electrode head from a relatively less rigid lead body in response to traction applied at the proximal end of the lead. The invention accomplishes this desired result by means of an inextensible or essentially inextensible conductor such as a straight wire or cabled conductor, coupled to a second electrode such as a ring electrode or coil electrode located on or adjacent the electrode head. In addition to being coupled to the second electrode, the inextensible conductor is mechanically interlocked with the electrode head so that traction forces applied to the proximal end of the lead body are applied by the inextensible conductor directly to the electrode head, rather than being applied to pull the electrode proximally away from or off of the electrode head. In a first embodiment of the invention, the inextensible conductor directly engages the electrode head, in a preferred embodiment at a point distal to the point of attachment of the conductor to the electrode. In a second embodiment the inextensible conductor engages an interlocking member which mechanically engages the electrode head and electrically engages the second electrode so that forces applied to the proximal end of the lead are applied directly to the electrode head, rather than being applied to the second electrode.

DETAILED DESCRIPTION OF THE PREFERRED EMBODIMENT OF THE INVENTION

Figure 1:
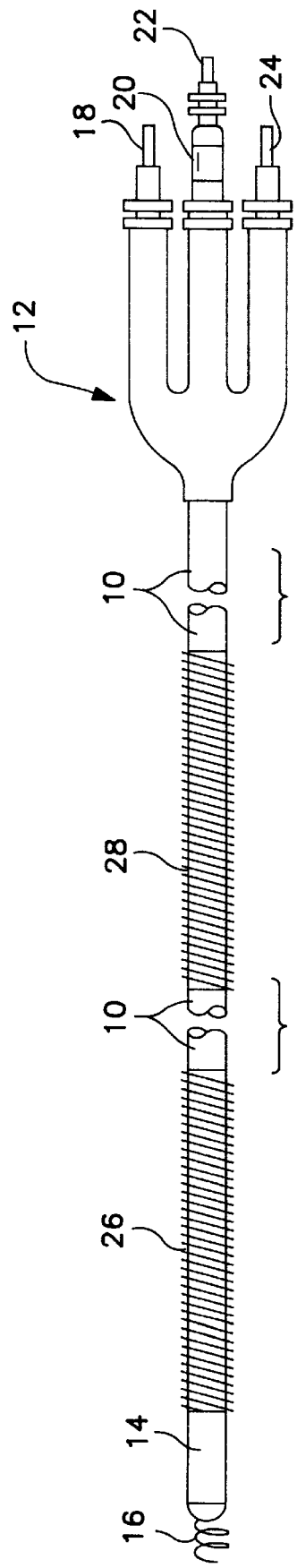
FIG. 1 is a plan view of a first embodiment of the invention.

FIG. 1 is a plan view of a lead incorporating a first embodiment of the invention. The lead is provided with an elongated insulative lead body 10 which may be fabricated of polyurethane or silicone rubber or other less rigid, elastic, relatively softer biocompatible plastic. The lead body carries at its distal end an insulative electrode head 14, which may also be fabricated of a relatively more rigid biocompatible plastic, such as a polyurethane and which carries an advanceable helical electrode 16. At its proximal end, the lead carries a trifurcated connector assembly 12 provided with two connector pins 18 and 24, each coupled to one of two elongated defibrillation electrodes coils 26 and 28. Connector assembly 12 also carries an IS-1 compatible, in-line connector assembly provided with a connector ring 20 which is coupled to defibrillation electrode coil 26 and a connector pin 22 coupled to helical electrode 16.

Figure 2:
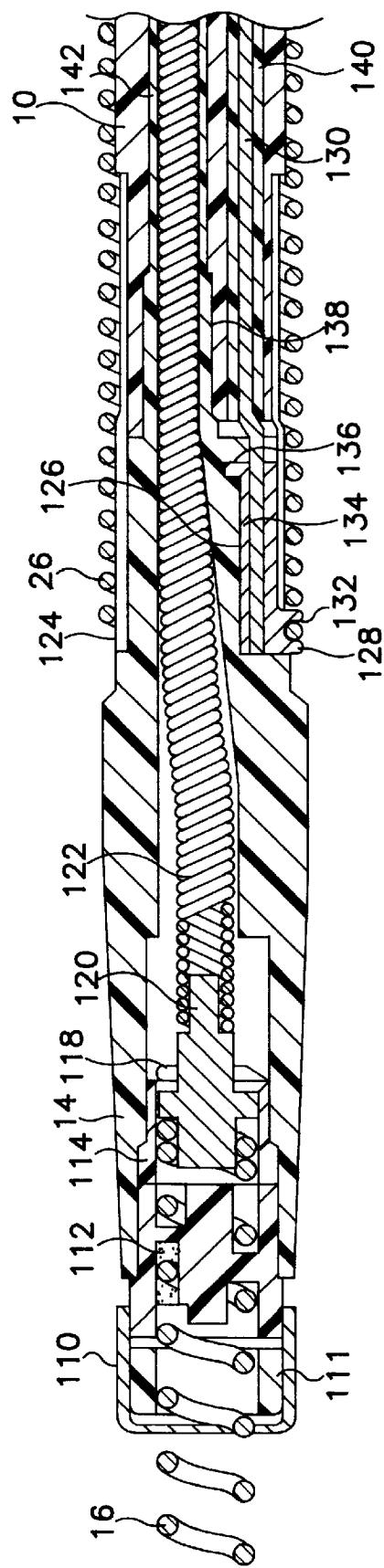
FIG. 2 is a sectional view through the distal portion of the lead illustrated in FIG. 1.

FIG. 2 is a cross-sectional view of the distal portion of the lead. The electrode head 14 is provided with a longitudinal internal lumen open to the distal end of the electrode head, out of which helical electrode 16 is advanced. Helical electrode 16 is mechanically and electrically coupled to conductive member 120 which is in turn mechanically and electrically coupled to coiled conductor 122, which may be fabricated of a biocompatible metal such as MP35N alloy, silver cored MP35N alloy or the like. Also located within the internal lumen of electrode head 14 is a helical guide member 112, fabricated of biocompatible plastic and configured such that upon rotation of coiled conductor 122, helical electrode 16 is advanced from or retracted into electrode head 14. At the distal end of electrode head is a monolithic controlled release device 111 which may correspond to that disclosed in U.S. Pat. No. 4,972,848 issued to DiDomenico et al., all incorporated by reference in its entirety. Cap member 110 serves to retain monolithic controlled release device 111 on the distal end of the helical guide member 112. A metal radio-opaque marker 114 is also provided and can be used to flouroscopically determine the relative degree of advancement of helical electrode 16.

Lead body 10 is a multi-lumen polymeric tube, mounted to the proximal end of electrode head 114. A tubular extension 138 is mounted within an internal lumen of lead body 10, through which coiled conductor 122 passes. A Teflon sleeve 142 surrounds coiled conductor 122, providing for increased ease of rotation of coiled conductor 122. In a second lumen within lead body 10 is a cabled conductor 130 of the type disclosed in U.S. Pat. No. 5,584,873 issued to Shoberg et al., incorporated herein by reference in its entirety. A second Teflon sleeve 140 surrounds conductor 130. Conductor 130 is crimped within a cross-groove crimp sleeve 128 corresponding generally to that disclosed in allowed pending U.S. patent application Ser. No. 08/657,577, filed by Boser et al. on Jun. 7, 1996, also incorporated herein by reference in its entirety. Crimp sleeve 128 is welded to the distal end of defibrillation electrode 126 along cross-groove 132, as described in the above cited Boser et al. patent application.

Cross-groove crimp sleeve 128 is mounted within a recess 126 formed in the proximal end of electrode head 14. Proximal movement of cross-groove crimp sleeve 128 relative to electrode head 14 is prevented by means of a flange or shoulder 136, not present in the crimp sleeve of the Boser et al application, which engages a corresponding groove formed within the proximal end of electrode head 14. Surrounding the proximal end of electrode head 14 and retaining cross-bore crimp sleeve 128 within the recess of the connector head 14 is a biocompatible plastic tube 124 which may be fabricated, for example, of silicone rubber. Sleeve 124 extends around the exterior periphery of lead body 10, further assisting in joining lead body 10 to electrode head 14. Sleeve 124 may be adhesively attached to electrode head 14 and lead body 10 if desired.

Conductor cable 130 is coupled at its proximal end to connector pin 18 and is additionally coupled to connector ring 20, allowing for delivery of defibrillation pulses to electrode 26 by means of pulses applied to connector pin 18 and allowing for bipolar sensing of cardiac electrograms using electrodes 16 and 26 to form what has come to be known as an "integrated bipolar" electrode pair. Because conductor 30 extends from the connector assembly at the proximal end of the lead to the electrode head, a mechanical interconnection of the connector assembly to the electrode head is provided, so that traction forces applied to the proximal end of the lead do not tend to pull the lead body 10 or coil electrode 122 away from or off of the proximal end of the electrode head 14. This mechanical interconnection is particularly valuable in conjunction with prevention of separation of the electrode head 14 from the lead body 10 resulting in exposure of coiled conductor 122 in conjunction with removal of a lead which has been implanted a sufficient time to allow for growth of fibrotic tissue affixing electrode head 14 to the interior surface of the heart.

Figure 3:
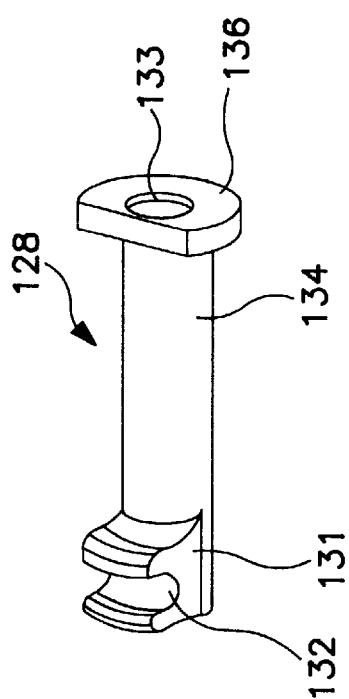
FIG. 3 is a perspective view of the interlocking member of the lead illustrated in FIGS. 1 and 2.

FIG. 3 is a perspective view of cross-groove crimp sleeve 128, which generally takes the form of a cylindrical sleeve 134 carrying a laterally outward projecting portion 131 in which cross groove 132 is formed. An elongated lumen 133 extends through the length of the cross-bore crimp sleeve 128, allowing for insertion of conductor cable 130 (FIG. 2). Conductor cable 130 is retained within cross-bore crimp sleeve 128 by means of crimps applied along the cylindrical section 134. Flange or shoulder 136 is also visible in this view, extending laterally and inwardly of the outwardly projecting portion 131. Flange or shoulder 132 serves as a mechanism by which traction forces applied on the proximal end of the lead may be imparted to the electrode head 14, in turn preventing separation of the electrode head 14 from lead body 10 during extraction of the lead.

Figure 4:
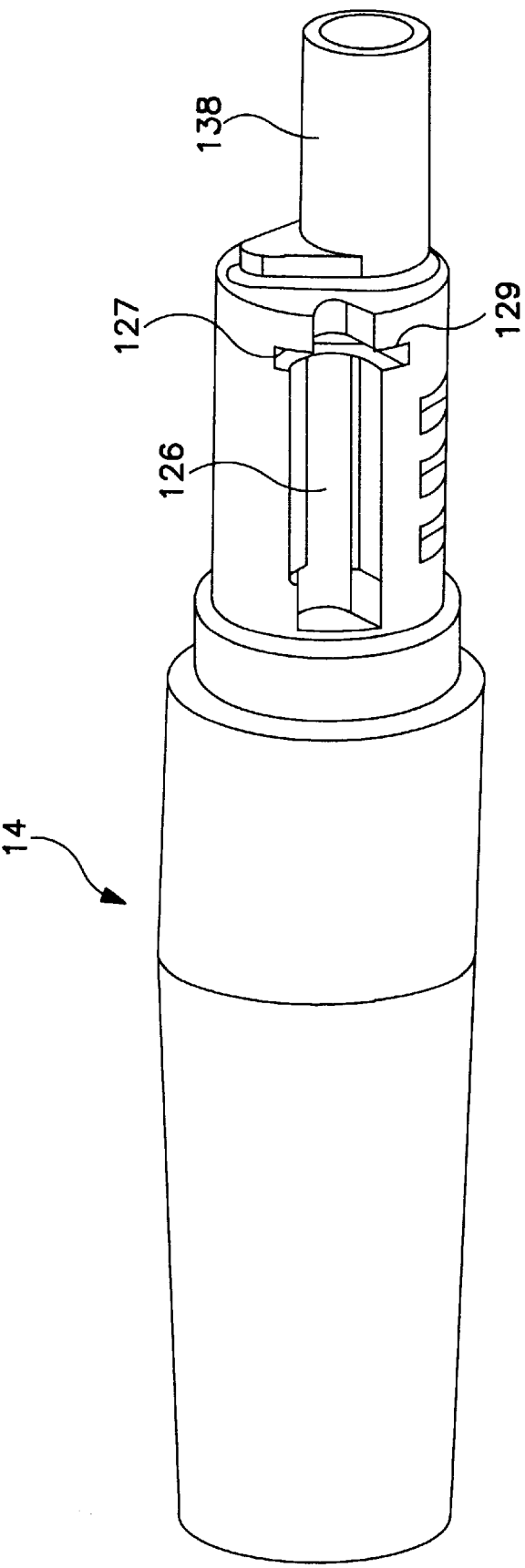
FIG. 4 is a perspective view of the electrode head member of the lead illustrated in FIGS. 1 and 2.

FIG. 4 is a perspective view of the electrode head 14 illustrating the configuration of recess 126 in which crossgrove crimp sleeve 128 is located. In this view, it can be seen that the recess 126 is provided with a slot 127 corresponding to shoulder or flange 136. The distally facing interior surface 129 of slot 127 engages the proximally facing surface of flange or shoulder 136, allowing for application of proximally directed traction force to the electrode head 14 via conductor 130. The configuration of extension 138, which is inserted into lead body 10, as illustrated in FIG. 2, is also apparent in this view.

Figure 5:
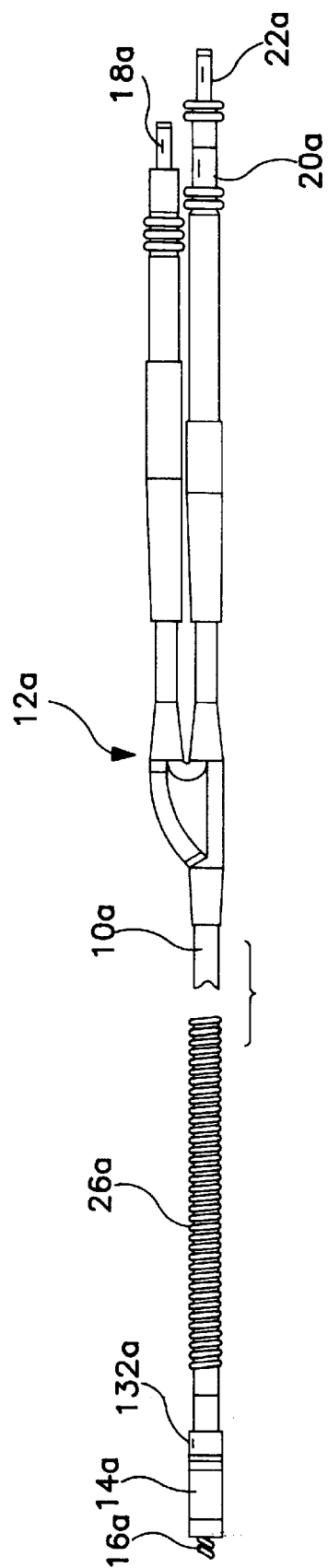
FIG. 5 is a plan view of a second embodiment of the invention.

FIG. 5 is a plan view of a lead incorporating a second embodiment of the invention. The lead is provided with an elongated insulative lead body 10a which may be fabricated of polyurethane or silicone rubber or other biocompatible elastic, relatively softer plastic. The lead body carries at its distal end an insulative electrode head 14a, which may also be fabricated of relatively more rigid biocompatible plastic and which carries an advanceable helical electrode 16a. At its proximal end, the lead carries a bifurcated connector assembly 12a provided with a connector pin 18a, each coupled to elongated defibrillation electrodes coil 26. Connector assembly 12a also carries an IS-1 compatible, in-line connector assembly provided with a connector ring 20a which is coupled to ring electrode 132a and a connector pin 22a coupled to helical electrode 16a.

Figure 6:
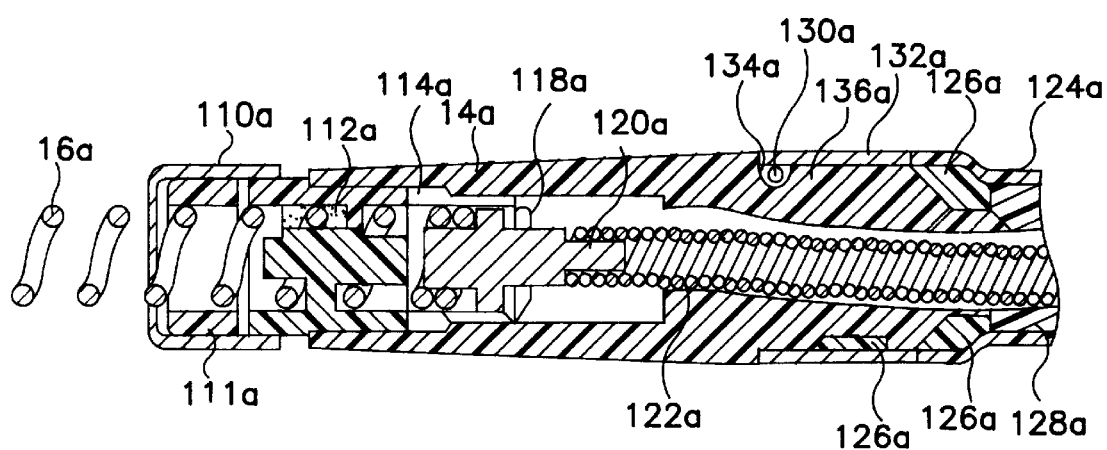
FIG. 6 is a sectional view through the distal portion of the lead illustrated in FIG. 5.

FIG. 6 is a cross-sectional view of the distal portion of the lead. The electrode head 14a is provided with a longitudinal internal lumen open to the distal end of the electrode head, out of which helical electrode 16a is advanced. Helical electrode 16a, conductive member 120a, coiled conductor 122a, helical guide member 112a, monolithic controlled release device 111a, cap member 110a and metal radioopaque marker 114a correspond to helical electrode 16, conductive member 120, coiled conductor 122, helical guide member 112, monolithic controlled release device 111, cap member 110 and metal radio-opaque marker 114 of the lead illustrated in FIGS. 1–4.

Lead body 10a is a multi-lumen polymeric tube, mounted to the proximal end of electrode head 114a. Coiled conductor 122a passes through an internal lumen of lead body 10a. In a second lumen within lead body 10a is a cabled conductor 130a, corresponding to cabled conductor 130 of the lead illustrated in FIGS. 1–4. Cabled conductor 130 a exits lead body 10a an passes distally alongside a block 136a, molded as part of electrode head 14a, turns and passes through groove 134 a molded into electrode head 14a and the passes proximally alongside block 136a to the point it is attached to ring electrode 132a. The inter-relation of conductor 130a and electrode head 14a are illustrated more clearly in FIG. 7, discussed below.

Conductor cable 130a is mechanically and electrically coupled at its proximal end to connector ring 20a (FIG. 5), and thereby to the proximal end of the lead. Bipolar pacing and bipolar sensing of cardiac electrograms may be accomplished using electrodes 16a and 132a. The extension of conductor 130a from the connector assembly at the proximal end of the lead to the electrode head provides for a mechanical interconnection of the connector assembly to the electrode head, so that traction forces applied to the proximal end of the lead do not tend to pull the lead body 10a or electrode 132a away from or off of the proximal end of the electrode head 14a. This mechanical interconnection is particularly valuable in conjunction with prevention of separation of the electrode head 14a from the lead body 10a resulting in exposure of coiled conductor 122a in conjunction with removal of a lead which has been implanted a sufficient time to allow for growth of fibrotic tissue affixing electrode head 14a to the interior surface of the heart.

Figure 7:
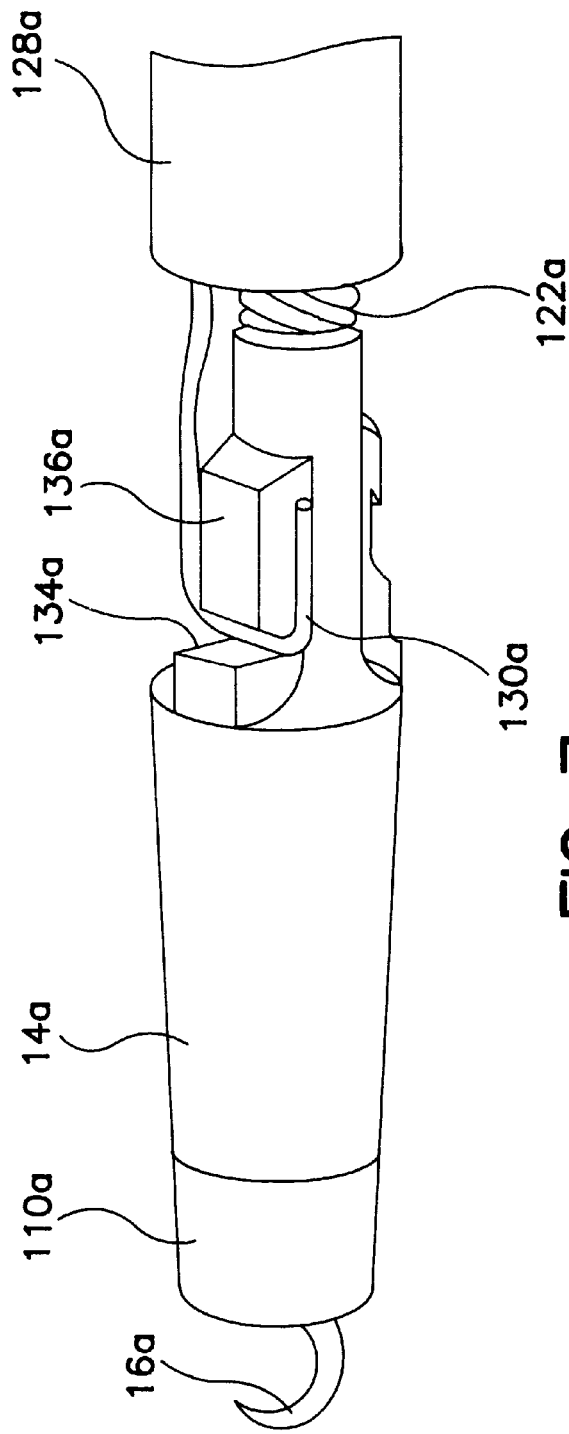
FIG. 7 is a perspective view illustrating the inter-relation of the electrode head member and inextensible conductor of the lead illustrated in FIGS. 5 and 6.

FIG. 7 is a perspective view of the portions of the distal end of the lead illustrated in FIGS. 5 and 6. In this view the configuration of the electrode head, 14a, block 136a and conductor 130a is more clearly visible. Conductor 130a extends distally alongside block 136a, turns laterally to pass through groove 134a and the extends proximally to the point at which is coupled to ring electrode 132a (FIG. 6) by means of a stake or crimp. Traction forces applied to the conductor 130a are applied to the electrode head 14a by means of block 136a. To the extent that forces are applied to electrode 132a, they tend to pull it distally, onto the electrode head rather than tending to pulling the electrode off of the electrode head.

Figure 8:
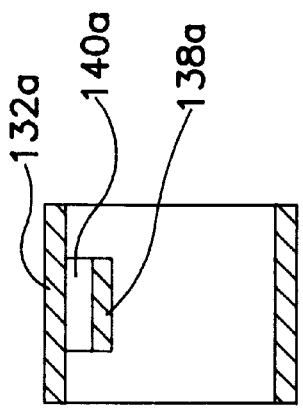
FIG. 8 is a sectional view through the ring electrode of the lead illustrated in FIGS. 5 and 6.

FIG. 8 is a sectional view through electrode 132a. Electrode 132 takes the form of a cylindrical ring having an internal projection 138a which is provided with an internal bore 140a. The uninsulated end of conductor 130a (FIG. 7) is inserted in the distal end of bore 140a and the conductor is staked therein to electrically and mechanically couple it to the electrode.

While the present invention is particularly useful in the context of leads as illustrated in which the electrode head carries an advanceable helical electrode, the invention may also be practiced in conjunction with leads in which the electrode carried by the head is fixedly mounted and/or does not take the form of a helix. Similarly, while the lead body as illustrated takes the form of a multi-lumen tube, the invention may also be practiced in the context of leads having a coaxial, multiple lumens produced using nested plastic tubes or other lead body configurations. As such, the above disclosure should be considered exemplary rather than limiting with regard to the scope of the following claims.

In conjunction with the above specification, we claim:

1. An implantable electrical lead comprising:

a rigid, insulative electrode head carrying a helical electrode;

an elongated insulative lead body less rigid than said electrode head, having a proximal end and a distal end coupled to the electrode head and having an inextensible conductor therein, mechanically coupled to the proximal end of the lead;

a coiled conductor mounted within the lead body, coupled to the helical electrode;

a second electrode mounted to said lead body adjacent the electrode head, coupled to the inextensible conductor; and means for interconnecting the inextensible conductor to the electrode head such that proximally directed traction forces applied to the proximal end of the lead body are applied to the head by the inextensible conductor and not by the second electrode.

2. An implantable electrical lead comprising:

a rigid, insulative electrode head carrying a first electrode;

an elongated insulative lead body less rigid than said electrode head, having a proximal end and a distal end coupled to the electrode head having an inextensible conductor therein, mechanically coupled to the proximal end of the lead;

a coiled conductor mounted within the lead body, coupled to the first electrode;

a second electrode mounted to said lead body adjacent the electrode head, coupled to the inextensible conductor; and means for interconnecting the inextensible conductor to the electrode head such that traction forces applied to the proximal end of the lead body are applied to the electrode head by the inextensible conductor and not by the second electrode wherein the inextensible conductor is mechanically coupled to the second electrode at a first point and wherein the interconnecting means comprises a groove formed in the electrode head, located distal to said first point and wherein the inextensible conductor extends distally to the groove, passes through the groove and then extends proximally to the first point.

3. A lead according to claim 1 wherein the inextensible conductor is mechanically coupled to the second electrode at a first point and wherein the interconnecting means comprises a groove formed in the electrode head, located distal to said first point and wherein the inextensible conductor extends distally to the groove, passes through the groove and then extends proximally to the first point.

4. A lead according to claim 1 or claim 2 or claim 3 wherein the second electrode is a ring electrode mounted to the electrode head.

5. A lead according to claim 4 wherein the inextensible conductor is a stranded conductor.

6. A lead according to claim 5 wherein the inextensible conductor is staked to the second electrode.

7. A lead according to claim 1 or claim 2 or claim 3 wherein the inextensible conductor is a stranded conductor.

8. A lead according to claim 7 wherein the inextensible conductor is staked to the second electrode.

* * * * *